(12) United States Patent
Wear et al.

(10) Patent No.: US 10,499,873 B2
(45) Date of Patent: Dec. 10, 2019

(54) SYSTEM AND METHOD FOR PERFORMING A BONE DENSITY SCAN OF A PATIENT

(71) Applicant: General Electric Company, Schenectady, NY (US)

(72) Inventors: James Wear, Madison, WI (US); Serge Muller, Buc (FR); Randall Payne, Madison, WI (US); Paul Markwardt, Madison, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 433 days.

(21) Appl. No.: 15/385,172

(22) Filed: Dec. 20, 2016

(65) Prior Publication Data

US 2018/0168533 A1    Jun. 21, 2018

(51) Int. Cl.
*A61B 6/00* (2006.01)

(52) U.S. Cl.
CPC .............. *A61B 6/54* (2013.01); *A61B 6/4035* (2013.01); *A61B 6/482* (2013.01); *A61B 6/505* (2013.01); *A61B 6/4441* (2013.01)

(58) Field of Classification Search
CPC ......... A61B 6/4241; A61B 6/482; A61B 6/54; A61B 6/5205; A61B 6/4035; A61B 6/4441
See application file for complete search history.

(56) References Cited

U.S. PATENT DOCUMENTS

| | | | |
|---|---|---|---|
| 5,054,048 A | 10/1991 | Wang | |
| 5,081,582 A | 1/1992 | Araki et al. | |
| 5,400,378 A | 3/1995 | Toth | |
| 5,696,807 A | 12/1997 | Hsieh | |
| 5,838,765 A * | 11/1998 | Gershman | A61B 6/0421 378/196 |
| 6,438,201 B1 * | 8/2002 | Mazess | A61B 6/405 378/108 |
| 7,068,750 B2 | 6/2006 | Toth et al. | |
| 7,706,508 B2 | 4/2010 | Arenson et al. | |
| 8,165,266 B2 | 4/2012 | Wear et al. | |

* cited by examiner

*Primary Examiner* — Don K Wong
(74) *Attorney, Agent, or Firm* — Grogan, Tuccillo & Vanderleeden, LLP (57) ABSTRACT

A system for performing a bone density scan of a patient is provided. The system includes a radiation source operative to emit a radiation beam, a radiation detector operative to receive the radiation beam and generate an output signal based at least in part on the received radiation beam, and a controller in electronic communication with the radiation source and the radiation detector and operative to generate at least one of a bone mineral content measurement of the patient, a bone mineral density measurement of the patient, a body composition measurement of the patient, and a body thickness measurement of the patient. The controller is further operative to regulate the radiation beam such that a flux of the radiation beam at the radiation detector is within a target flux range.

14 Claims, 4 Drawing Sheets

SYSTEM AND METHOD FOR PERFORMING A BONE DENSITY SCAN OF A PATIENT

BACKGROUND

Technical Field

Embodiments of the invention relate generally to medical diagnostic imaging systems, and more specifically, to a system and method for performing a bone density scan of a patient.

Discussion of Art

Many bone density imaging systems include an x-ray source that emits a collimated beam of dual-energy x-rays to image an object/patient. In such systems, an x-ray detector is positioned with respect to the x-ray source so as to receive the x-rays that have passed through the object. The amount of x-rays received by the detector during a given duration of time is known as flux. The x-ray source and the x-ray detector typically move in unison along a path that traverses the object during a scan, and the detectors of many such systems typically output/produce electrical signals in response to the received x-rays. In other words, many such detectors modulate an electrical output signal in response to the level of flux as sensed/determined by the detectors. In many bone density imaging systems, the electrical output signal of the detector is usually digitized and subsequently used by the bone density imaging system to generate scanned images of the object. Measurements of the x-ray absorption by the imaged object at two different x-ray energies, i.e., the changes in the flux at the x-ray detector, reveals information about the composition and/or density of the object as decomposed into two selected basis materials, e.g., fat/soft tissue and bone.

In many bone density imaging systems, the beam of dual-energy x-rays is generated/emitted by the x-ray source at a constant intensity throughout a scanning period/procedure. In many such systems, the constant intensity of the beam assumes that the thickness of the object is relatively constant/uniform. With respect to human patients, the constant intensity of the beam may be selected based upon a standard thickness of the scanned site for a typical patient profile for a given height and weight. For objects that do not have a constant/uniform thickness, however, a constant intensity beam results in changes in flux that are too extreme to be useful in calculating density. Thus, as some patients have non-standard site thicknesses, i.e., thicknesses that do not closely match a typical patient profile for a given height and weight, the transmitted flux to the detector is usually sub-optimal.

Further, many x-ray detectors become saturated, i.e., cease to function properly, if the flux at the x-ray detectors is too high. As such, using a constant beam intensity becomes highly problematic during "whole-body" scans where the x-ray beam must typically scan "in air," which as used herein, refers to a situation where a radiation beam passes from a radiation source, to include filters associated with control/modulation of the beam, to a radiation detector without passing through an object intended to be imaged by the beam, i.e., the radiation beam passes through the air. For example, using a low constant beam intensity to avoid saturation of the x-ray detector when the beam is scanning in air results in insufficient flux when the beam passes over thick parts of the object being scanned. Conversely, using a high constant beam intensity to ensure sufficient flux when the beam is passing over thick parts of the objects results in saturation of the x-ray detector when the beam scans in air, i.e., the output signal of the detector no longer accurately reflects the changes in density.

What is needed, therefore, is an improved system and method for performing a bone density scan of a patient.

BRIEF DESCRIPTION

In an embodiment, a system for performing a bone density scan of a patient is provided. The system includes a radiation source operative to emit a radiation beam and to move along a scanning path, a radiation detector operative to move along the scanning path so as to receive the radiation beam and generate an output signal based at least in part on the received radiation beam, and a controller in electronic communication with the radiation source and the radiation detector and operative to generate at least one of a bone mineral content measurement of the patient, a bone mineral density measurement of the patient, a body composition measurement of the patient, and a body thickness measurement of the patient. The controller is further operative to regulate the radiation beam while the radiation source and the radiation detector move along the scanning path such that a flux of the radiation beam at the radiation detector is within a target flux range.

In another embodiment, a method for performing a bone density scan of a patient is provided. The method includes: emitting a radiation beam via a radiation source that moves along a scanning path and is in electronic communication with a controller; receiving the emitted radiation beam via a radiation detector that moves along the scanning path and is in electronic communication with the controller; regulating the radiation beam via the controller such that a flux of the radiation beam at the radiation detector is within a target flux range; and generating at least one of a bone mineral content measurement of the patient, a bone mineral density measurement of the patient, a body composition measurement of the patient, and a body thickness measurement of the patient via the controller based at least in part on an output signal generated by the radiation detector.

In yet another embodiment, another method for performing a bone density scan of a patient is provided. The method includes: emitting a radiation beam via a radiation source that moves along a scanning path and is in electronic communication with a controller; receiving the emitted radiation beam via a radiation detector that moves along the scanning path and is in electronic communication with the controller; detecting when the radiation beam is scanning in air via the controller; and generating at least one of a bone mineral content measurement of the patient, a bone mineral density measurement of the patient, a body composition measurement of the patient, and a body thickness measurement of the patient via the controller based at least in part on an output signal generated by the radiation detector.

DRAWINGS

The present invention will be better understood from reading the following description of non-limiting embodiments, with reference to the attached drawings, wherein below.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process.

Further, while the embodiments disclosed herein are described with respect to dual-energy x-ray absorptiometry ("DEXA" or "DXA"), it is to be understood that embodiments of the present invention may be applicable to other types of medical imaging systems. Further still, as will be appreciated, embodiments of the present invention related imaging systems may be used to analyze tissue generally and are not limited to human tissue.

Figure 1:
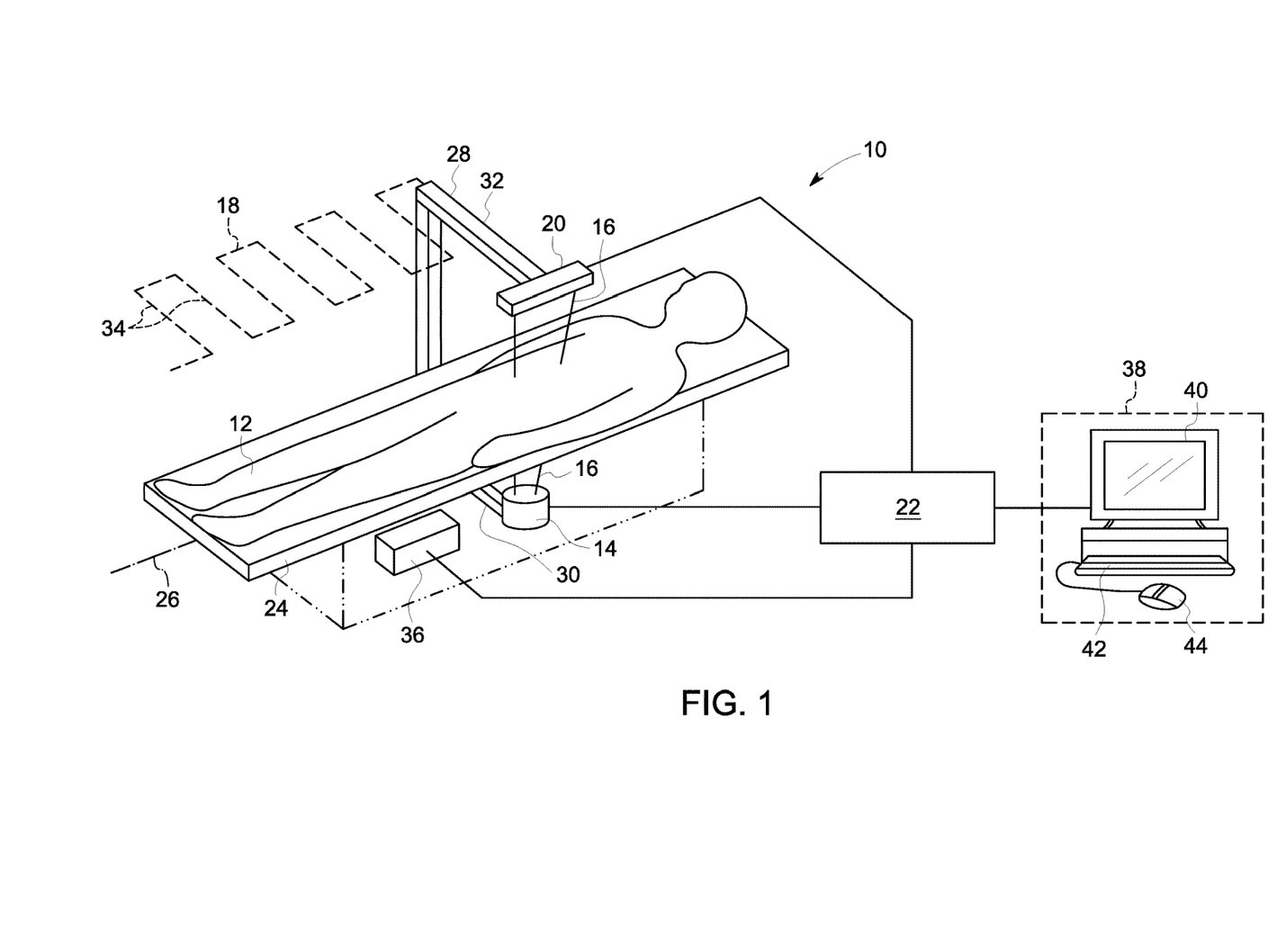
FIG. 1 is a perspective view of a system for performing a bone density scan of a patient in accordance with an embodiment of the invention.

Referring now to FIG. 1, the major components of a system 10 for performing a bone density scan of an object/patient 12 are shown. As will be appreciated, in embodiments, the system 10 may be a DEXA system that functions as a dual energy bone densitometer capable of performing bone densitometry. Accordingly, in embodiments, the bone density scan performed by the system 10 may be used to generate a bone mineral content ("BMC") measurement, a bone mineral density ("BMD") measurement, body composition measurement, and/or a body thickness measurement. In embodiments, the BMD may be calculated by dividing the BMC by the area of bone imaged. During operation of the system 10, in accordance with embodiments of the invention, an x-ray beam with broadband energy levels is utilized to scan the object/patient 12 to image the patient's bones. The acquired scanned images may then be used to diagnose a medical condition such as osteoporosis. In embodiments, the scanned images may be generated in part from determined bone density information acquired during a dual-energy x-ray scan.

Accordingly, and as shown in FIG. 1, the system 10 includes a radiation source 14 operative to emit a radiation beam 16 and to move along a scanning path 18, a radiation detector 20 operative to move along the scanning path 18 and to receive the radiation beam 16, and a controller 22 in electronic communication with the radiation source 14 and the radiation detector 20. As will be described in greater detail below, the controller 22 is operative to regulate the radiation beam 16 while the radiation source 14 and the radiation detector 20 move along the scanning path 18 such that a flux of the radiation beam 16 at the radiation detector 20 is within a target flux range.

In embodiments, the system 10 may further include a patient table 24 for providing a horizontal surface for supporting the patient 12 in a supine or lateral position along a longitudinal axis 26, a support member 28, which in embodiments, may be a C-arm having a lower end 30 and an upper end 32, the lower end 30 being positioned beneath the table 24 so as to support the radiation source 14, and the upper end 32 positioned above the table 24 so as to support the radiation detector 20. While the radiation source 14 and the radiation detector 20 are shown in FIG. 1 as being below and above the patient 12, respectively, it will be understood that the positions of the radiation source 14 and the radiation detector 20 may be reversed such that the radiation source 14 and the radiation detector 20 are above and below the patient 12, respectively. In embodiments, the radiation detector 20 may be fabricated, for example, as a multi-element cadmium-tellurium ("CdTe") detector that provides for energy discrimination. In embodiment, the radiation detector 20 may also be a single or multi-element scintillator with photomultiplication for energy discrimination.

As stated above, the radiation source 14 and the radiation detector 20 move along the scanning path 18 so as to trace a series of transverse scans 34 of the patient 12, during which dual energy radiation, e.g., x-ray, data is collected by the radiation detector 20. In embodiments, the transverse scanning procedure generates either a single scan image or a quantitative data set from a plurality of scanned images acquired across the patient 12, wherein the radiation source 14 and the radiation detector 20 are either longitudinally aligned with the superior-inferior axis of the patient 12 or transversely from one side of patient to another, e.g., left to right. As will be appreciated, scanning the patient 12 using a transverse motion facilitates minimizing the time between acquisitions of adjacent scanned images since the transverse direction across the patient 12 is shorter than the longitudinal direction across the patient 12. Thus, transverse scanning may reduce the severity of motion artifacts between the scanned images, which in turn may further provide for improved accuracy in merging acquired scanned images. As will be appreciated, however, in embodiments, the scanning path 18 may be a series of longitudinal scans.

In certain embodiments, the transverse scanning motion may be produced by actuators (not shown) controlled via a translation controller 36 which may be in electronic communication with, or form part of, the controller 22. During operation, the radiation source 14 produces/generates/emits the radiation beam 16, which in embodiments, may have a fan shape having a plane that is parallel to the longitudinal axis 26. In other embodiments, however, the radiation beam 16 may have a fan shape having a plane that is perpendicular to the longitudinal axis 26. Further, in embodiments, the scanning pattern/path 18 may be configured such that there is some overlap (e.g., 10% of the scanned surface area) between successive scan lines 34 of the radiation beam 16. As will be understood, in embodiments, the radiation beam 16 may have a pencil shape, a cone shape, and/or other shapes appropriate for scanning the patient 12.

In embodiments, the radiation source 14, the radiation detector 20, and the translation controller 36 may be controlled via the controller 22. The controller 22 may electronically communicate with a terminal 38 that includes a display 40, a keyboard 42, and a cursor control device 44, e.g., a mouse, that provide for the input and output of information, e.g., text, images, and/or other forms of data, into and out of the system 10. In embodiments, the controller 22 may be located remotely from the terminal 38. In other embodiments, the controller 22 may be integrated into the terminal 38. In embodiments, the controller 22 is adapted to perform one or more processing operations. For example, the bone and tissue information acquired by the radiation detector 20 may be processed and displayed in real-time during a scanning session as the data is received by the controller 22 from the radiation detector 20. The display 40 may include one or more monitors that present information concerning the patient 12, e.g., the scanned images and bone length images, to the operator for diagnosis and analysis. The displayed images may be modified and the display settings of the display 40 also manually adjusted using the keyboard 42, the mouse 44, and/or a touch screen icon on the display 40.

As will be further understood, the system 10 may be configured to operate in a dual energy mode, a single energy mode, or a broadband mode. In single energy mode, the radiation beam 16 includes a single narrow band of energies, e.g., 20-150 keV. The single energy mode may provide for high resolution scanned images. In dual energy mode, the radiation beam 16 includes two or more narrow bands of energies, which may be emitted simultaneously or in succession. Dual energy mode may be utilized to acquire a scan image of the entire body of the patient 12 that includes information relating to the bones and tissues of the patient's 12 body, which in turn may be utilized to measure bone density and/or other bone and tissue characteristics or content. In broadband mode, the radiation beam 16 may include a single broad band of energies. As will be appreciated, the system 10 may be switchable between the various aforementioned modes.

Figure 2:
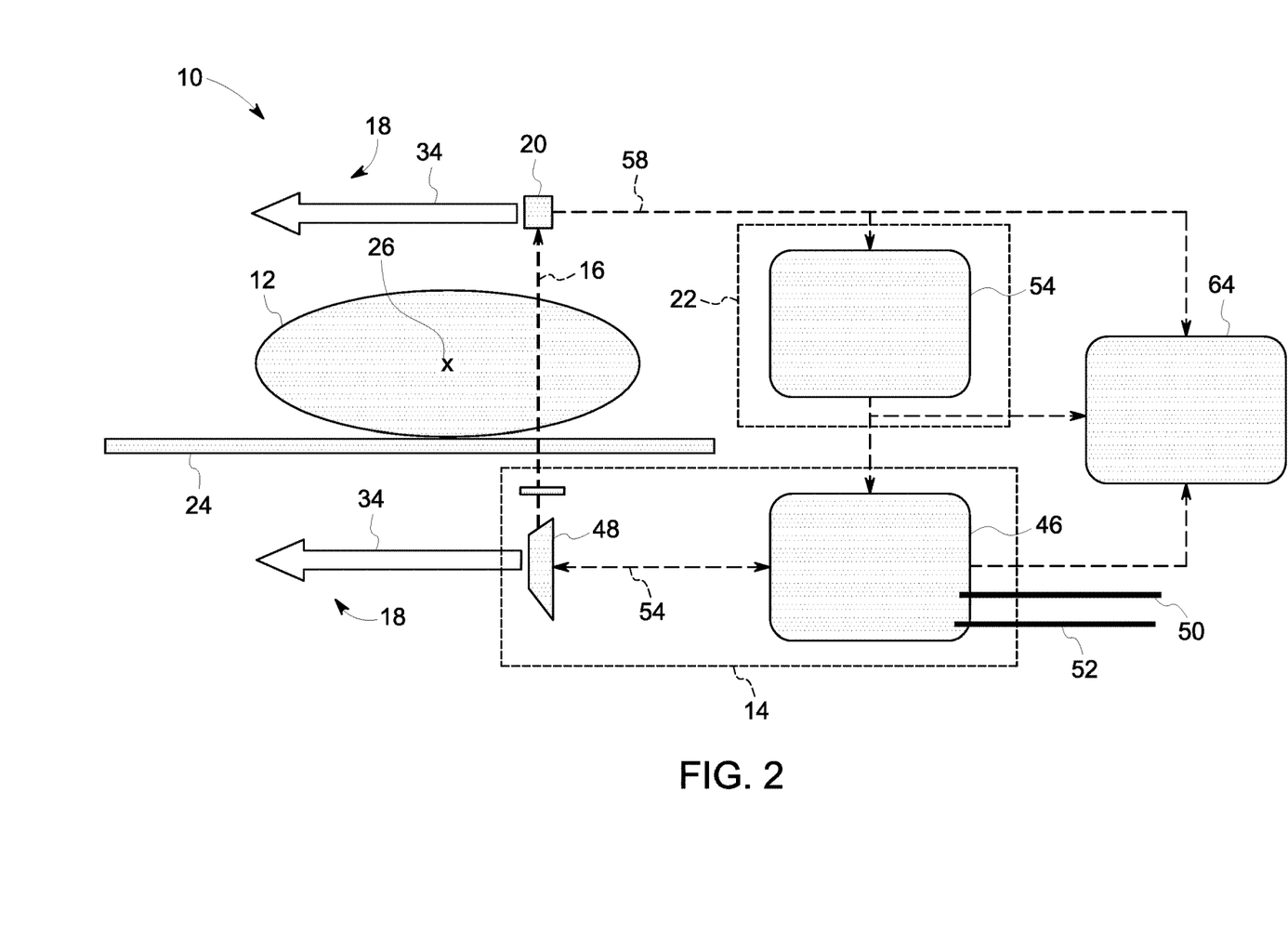
FIG. 2 is a block diagram of the system of FIG. 1 in accordance with an embodiment of the invention.

Turning now to FIG. 2, a block diagram of the system 10 is shown wherein the longitudinal axis 26 is depicted as extending out of the drawing sheet, e.g., FIG. 2, depicts a longitudinal view of the patient 12 laying down on the table 24. As shown in FIG. 2, in embodiments, the radiation source 14 may include a ray generator 46, a ray tube 48, a source current 50, and a source voltage 52. As such, in embodiments, the ray generator 46 produces/generates an electrical current based on the source current 50 and/or the source voltage 52. The generated electrical current is then fed to the ray tube 48, via an electrical connection 54, which produces the radiation beam 16. As will be appreciated, the intensity of the radiation beam 16 at the ray tube 48 is at least partially determined by the source current 50 and the source voltage 52. As such, in embodiments, the initial setting(s) of the source current 50 and/or the source voltage 52 may be based on one or more characteristics of the patient 12, e.g., height, weight, body mass index, and/or other appropriate characteristics. For example, in some embodiments, the initial settings of the source current 50 and/or the source voltage 52 may be based at least in part on a height-and-weight chart that correlates various heights and weights to initial settings for the source current 50 and/or the source voltage 52. As will be appreciated, in embodiments, the initial source current 50 may be between about 0.1 mA to 3 mA.

As will be understood, as the beam 16 moves along the scanning path, the flux at the radiation detector 20 changes. For example, in embodiments, when the beam 16 is fully to the right or to the left of the patient 12 such that the beam 16 does not pass through the patient 12, i.e., when the beam 16 is "scanning in air," the intensity of the beam 16 at the detector 20, i.e., the flux, is substantially the same as the intensity of the beam 16 at the tube 48. In other words, the patient's 12 body is not absorbing and/or deflecting rays/photons from the beam 16. As the beam 16 begins to move across the patient 12, e.g., right to left, some of the rays/photons within the beam 16 are either absorbed and/or deflected by the patient's 12 body such that the intensity of the beam 16 at the detector 20, e.g., the flux, is less than the intensity of the beam 16 at the tube 48. As the beam 16 continues to cross the patient 12, the flux of the beam 16 at the detector 20 varies as the thickness and the density of the patient's 12 body varies.

As stated above, in embodiments, the controller 22 regulates the radiation beam 16 while the radiation source 14 and the radiation detector 20 move along the scanning path 18 such that the flux, i.e., the intensity of the beam 16 at the detector 20, is within a target flux range. As will be appreciated, in embodiments, the controller 22 may regulate the beam 16 in real-time and/or the target flux range may be between about 20-100,000 counts/s. As used herein, the term "count" means the detection of a photon by the radiation detector 20, e.g., 100 counts/s means that the radiation detector 20 detected 100 photons from the radiation beam 16 over a duration of time lasting one (1) second.

As further shown in FIG. 2, the controller 22 may include a flux converter 54 that adjusts the intensity of the beam 16 based on an output signal 58 of the detector 20. In other words, in embodiments, the flux converter 54 converts the output signal 58 into a desired beam 16 intensity at the tube 48 based on a desired flux at the radiation detector 20. In embodiments, the flux converter 54 may adjust the intensity of the beam 16 via adjusting the source current 50 and/or the source voltage 52. For example, if the controller 22 determines that the flux at the detector 20 is too high, e.g., greater than or equal to 100,000 counts/s, the flux converter 54 may lower either the source current 50 and/or the source voltage 52. Conversely, if the controller 22 determines that the flux at the detector 20 is too low, e.g., less than or equal to 20 counts/s, the flux converter 54 may increase either the source current 50 and/or the source voltage 52.

As will be understood, in embodiments, the output signal 58 generated by the radiation detector 20 may be a voltage and/or current, to include both direct current ("DC") and alternating current ("AC"), signal modulated by the radiation detector 20 in response to the amount of flux of the beam 16 as measured/sensed by the radiation detector 20. A such, in embodiments, the output signal 58 may be an analogue or a digital signal that encodes the level of flux of the beam as measured/determined by the radiation detector 20. For example, in embodiments, the output signal 58 may encode the flux of the beam 16 at the radiation detector as a range between about 0.95 mA to 1.0 mA.

Figure 3:
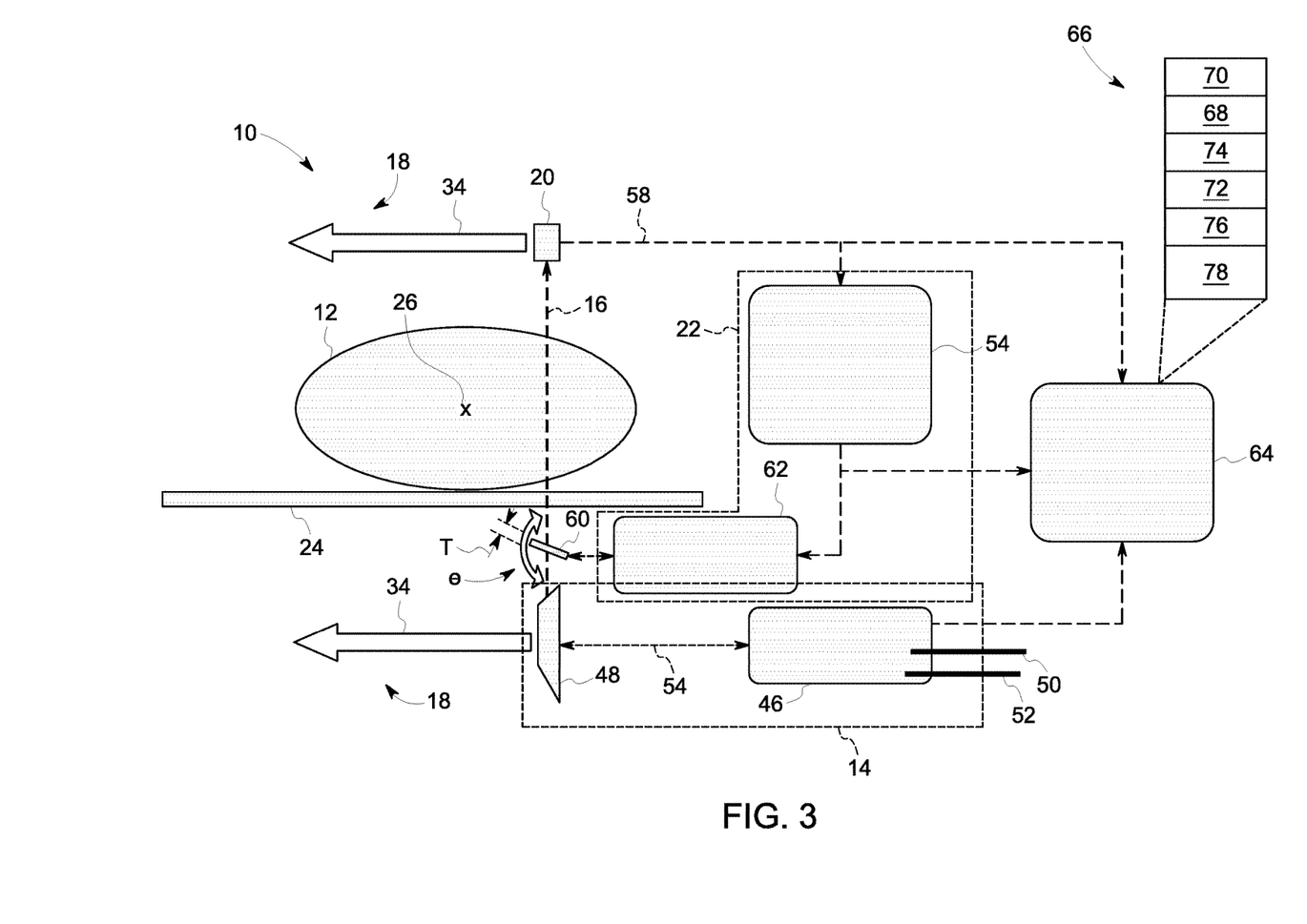
FIG. 3 is another block diagram of the system of FIG. 1, wherein the system includes a beam filter in accordance with an embodiment of the invention.

Moving now to FIG. 3, in embodiments, the system 10 may further include a beam filter 60 disposed between the radiation source 14 and the radiation detector 20 and operative to adjustably restrict a portion of the beam 16 from reaching the radiation detector 20, i.e., the beam filter 60 adjusts the intensity of the beam 16 via blocking, redirecting, and/or absorbing rays from the beam 16. As will be appreciated, in such embodiments, the controller 22 may further include a beam controller 62, which controls the beam filter 60. For example, the beam controller 62 may adjust, via an actuator such as a servo-motor, an angle Ø of orientation of the beam filter 60 which may alter the amount of rays of the beam 16 absorbed by the beam filter 60. In embodiments, the beam controller 62 adjust a thickness T of the beam filter 60 which may alter the amount of rays from of beam 16 absorbed by the beam filter 60. For example, in embodiments, beam filter 60 may include on or more segments that the controller 22 may move in and out of the path of the radiation beam 16, via solenoids or other appropriate actuators, so as to adjust the thickness T of the beam filter 60.

As will be understood, similar to the source current 50 and the source voltage 52, in embodiments, the initial angle Ø of orientation and/or the thickness T of the beam filter 60 may be based on one or more characteristics of the patient 12, e.g., height and/or weight.

As also shown in FIG. 3, in embodiments, the system 10 may further include a data recorder 64 in electronic communication with the controller 22 and operative to store one or more flux-to-variable-control readings 66. In embodiments, each of the flux-to-variable-control readings 66 may include a measurement 68 of the flux of the radiation beam 16 at the radiation detector 20 during a duration of time 70 corresponding to the flux-to-variable-control readings 66, a measurement 72 of the source current 50 during the duration of time 70, a measurement 74 of the source voltage 52 during the duration of time 70, a measurement 76 of the angle Ø of orientation of the beam filter 60, and/or a measurement 78 of the thickness T of the beam filter 60 during the duration of time 70. In embodiments, each of the flux-to-variable-control readings 66 may further include a data object, e.g., a timestamp, representing the duration of time 70. As will be appreciated, the flux-to-variable-control readings 66 allow the controller 22 to calibrate adjustments to the source current 50, source voltage 52, angle of orientation Ø, and/or thickness T to a desired beam 16 flux at the detector 20. In other words, the controller 22 may adjust the scaling between the output signal 58 and the adjustments to the source current 50, source voltage 52, and/or the beam filter 60.

Figure 4:
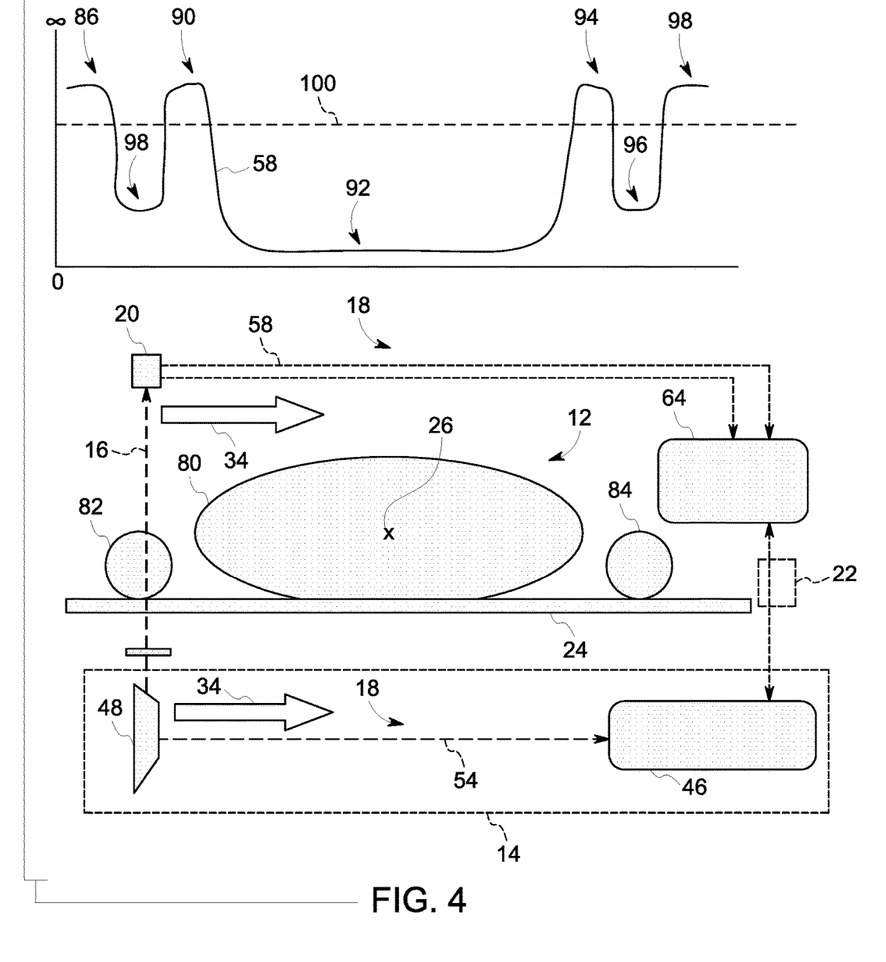
FIG. 4 is a block diagram of another system for performing a bone density scan of a patient in accordance with an embodiment of the invention.

Turning to FIG. 4, another block diagram of the system 10 is shown wherein the output signal 58 of the detector 20 has been drawn above the patient's main body 80, and the patient's left 82 and right 84 arms, such that variations in flux at the detector 20, as shown by the output signal 58, correspond to the regions of the patient 80, 82, and 84 shown below. For example, in embodiments, the radiation beam 16 may start scanning in air to the left of the patient's left arm 82 resulting in the output signal 58 having a value at/or near peak 86. The beam 16 may then continue to move right such that it passes through the patient's left arm 82 resulting in the output signal 58 having a value at/or near valley 88. As the beam 16 moves past the left arm 82, the beam 16 begins to again scan in air such that the output signal 58 has a value at/or near peak 90. The beam 16 may then continue to move right so as to pass through the patient's main body 80 resulting in the output signal 58 having a value at/or near valley 92. The beam 16 may then move past the main body 80 such that it again begins scanning in air wherein the output signal 58 has a value at/or near peak 94. The beam 16 may then move further to the right such that the beam 16 beings to pass through the patient's right arm 84 rustling in the output signal 58 having a value at/or near valley 96. Once past the patient's right arm 84, the beam 16 again begins to scan in air resulting in the output signal 58 having a value at/or near peak 98.

As will be understood, in embodiments, the controller 22 may be further adapted to determine when the beam 16 is scanning in air, and to remove/disregard the associated data from the output signal 58 of the detector 20 when constructing the scanned images and/or generating the bone mineral content measurement, the bone mineral density measurement, and/or the body thickness measurement of the patient, as discussed above. For example, in such embodiments, the controller 22 may detect when the output signal 58 of the detector 20 exceeds an upper flux threshold 100. As such, the controller 22 may discard all data within the output signal 58 of the detector 20 that falls above the upper flux threshold 100. In embodiments, the upper flux threshold 100 may correspond to an output signal 58 value greater than or equal to 1.0 mA.

Further, in embodiments, the controller 22 may directly monitor/sense/detect the value of the output signal 58 via a voltage and/or current sensor directly connected to a detector channel, e.g., a source electrode/pin of the radiation detector 20 that carries the output signal 58. In other embodiments, however, the controller 22 may indirectly monitor/sense/detect the value of the output signal 58 via a voltage sensor, current sensor, or other type of sensor connected to an electrical component, other than a detector channel of the radiation detector 20, which provides a reading/measurement that can be used by the controller 22 to derive the value of the output signal 58. As will be appreciated, indirect monitoring of the value of the output signal 58 reduces the chance that the output signal 58 will be altered, and therefore, in embodiments, provides for a more accurate method of obtaining the value of the output signal 58.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for performing a bone density scan of a patient is provided. The system includes a radiation source operative to emit a radiation beam and to move along a scanning path, a radiation detector operative to move along the scanning path so as to receive the radiation beam and generate an output signal based at least in part on the received radiation beam, and a controller in electronic communication with the radiation source and the radiation detector and operative to generate at least one of a bone mineral content measurement of the patient, a bone mineral density measurement of the patient, and a body thickness measurement of the patient. The controller is further operative to regulate the radiation beam while the radiation source and the radiation detector move along the scanning path such that a flux of the radiation beam at the radiation detector is within a target flux range. In certain embodiments, the controller regulates the radiation beam by adjusting at least one of a source current of the radiation source and a source voltage of the radiation source. In certain embodiments, the system further includes a data recorder in electronic communication with the controller and operative to store one or more flux-to-variable-control readings. In such embodiments, each of the flux-to-variable-control readings includes a measurement of the flux of the radiation beam at the radiation detector during a duration of time corresponding to the flux-to-variable-control reading, and at least one of a measurement of the source current during the duration of time and, a measurement of the source voltage during the duration of time. In such embodiments, the controller adjusts at least one of the source current and the source voltage based at least in part on the one or more flux-to-variable-control readings. In certain embodiments, the system further includes a beam filter disposed between the radiation source and the radiation detector and operative to adjustably restrict a portion of the radiation beam from reaching the radiation detector. In such embodiments, the controller regulates the radiation beam by adjusting the beam filter. In certain embodiments, the controller adjusts the beam filter via at least one of adjusting an angle of orientation of the beam filter and adjusting a thickness of the beam filter. In certain embodiments, the system further includes a data recorder in electronic communication with the controller and operative to store one or more flux-to-variable-control readings. In such embodiments, each of the flux-to-variable-control readings includes a measurement of the flux of the radiation beam at the radiation detector during a duration of time corresponding to the flux-to-variable-control reading, and at least one of a measurement of the angle of orientation during the duration of time, and a measurement of the thickness during the duration of time. In such embodiments, the controller adjusts at least one of the angle of orientation and the thickness based at least in part on the one or more flux-to-variable-control readings. In certain embodiments, the radiation beam is an x-ray beam. In certain embodiments, the x-ray beam includes x-rays of different energy levels.

Other embodiments provide for a method for performing a bone density scan of a patient. The method includes: emitting a radiation beam via a radiation source that moves along a scanning path and is in electronic communication with a controller; receiving the emitted radiation beam via a radiation detector that moves along the scanning path and is in electronic communication with the controller; regulating the radiation beam via the controller such that a flux of the radiation beam at the radiation detector is within a target flux range; and generating at least one of a bone mineral content measurement of the patient, a bone mineral density measurement of the patient, and a body thickness measurement of the patient via the controller based at least in part on an output signal generated by the radiation detector. In certain embodiments, regulating the radiation beam via the controller such that a flux of the radiation beam at the radiation detector is within a target flux range includes adjusting at least one of a source current of the radiation source and a source voltage of the radiation source via the controller. In certain embodiments, the method further includes obtaining one or more flux-to-variable-control readings via the controller, and storing, via the controller, the one or more flux-to-variable-control readings in a data recorder in electronic communication with the controller. In such embodiments, each of the flux-to-variable-control readings includes a measurement of the flux of the radiation beam at the radiation detector during a duration of time corresponding to the flux-to-variable-control reading, and at least one of a measurement of the source current during the duration of time, and a measurement of the source voltage during the duration of time. In such embodiments, adjusting at least one of the source current of the radiation source and the source voltage of the radiation source via the controller is based at least in part on the one or more flux-to-variable-control readings. In certain embodiments, regulating the radiation beam via the controller such that a flux of the radiation beam at the radiation detector is within a target flux range includes adjusting a beam filter via the controller, the beam filter disposed between the radiation source and the radiation detector and operative to restrict a portion of the radiation beam from reaching the radiation detector. In certain embodiments, adjusting a beam filter via the controller includes adjusting at least one of an angle of orientation of the beam filter, and a thickness of the beam filter via the controller. In certain embodiments, the method further includes obtaining one or more flux-to-variable-control readings via the controller, and storing, via the controller, the one or more flux-to-variable-control readings in a data recorder in electronic communication with the controller. In such embodiments, each of the flux-to-variable-control readings includes a measurement of the flux of the radiation beam at the radiation detector during a duration of time corresponding to the flux-to-variable-control reading, and at least one of a measurement of the angle of orientation during the duration of time, and a measurement of the thickness during the duration of time. In such embodiments, adjusting at least one of an angle of orientation of the beam filter, and a thickness of the beam filter via the controller is based at least in part on the one or more flux-to-variable-control readings. In certain embodiments, the radiation beam is an x-ray beam. In certain embodiments, the x-ray beam includes x-rays of different energy levels.

Yet still other embodiments provide for another method for performing a bone density scan of a patient. The method includes: emitting a radiation beam via a radiation source that moves along a scanning path and is in electronic communication with a controller; receiving the emitted radiation beam via a radiation detector that moves along the scanning path and is in electronic communication with the controller; detecting when the radiation beam is scanning in air via the controller; and generating at least one of a bone mineral content measurement of the patient, a bone mineral density measurement of the patient, and a body thickness measurement of the patient via the controller based at least in part on an output signal generated by the radiation detector. In certain embodiments, the controller disregards data within the output signal generated by the radiation detector when the radiation beam was scanning in air. In certain embodiments, detecting when the radiation beam is scanning in air via the controller includes directly monitoring the output signal. In certain embodiments, detecting when the radiation beam is scanning in air via the controller includes indirectly monitoring the output signal.

Accordingly, as will be appreciated, by utilizing a controller that regulates the radiation beam such that the flux of the beam at the radiation detector is within a target flux range during a scanning procedure, some embodiments of the invention provide for a DEXA system that has improved flux uniformity throughout the scanning procedure. Accordingly, some embodiments of the invention provide for a DEXA system that generates scanned images of a higher quality than existing systems.

Further, by detecting in real-time when the radiation beam is scanning in air, some embodiments of the invention provide for improved image segmentation, i.e., the identification of hard tissue, e.g., bone, from soft tissue, e.g., fat.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for performing a bone density scan of a patient comprising:
   a radiation source operative to emit a radiation beam and to move along a scanning path;
   a radiation detector operative to move along the scanning path so as to receive the radiation beam and generate an output signal based at least in part on the received radiation beam;
   a controller in electronic communication with the radiation source and the radiation detector and operative to generate at least one of a bone mineral content measurement of the patient, a bone mineral density measurement of the patient, a body composition measurement of the patient, and a body thickness measurement of the patient;
   a beam filter disposed between the radiation source and the radiation detector and operative to adjustably restrict a portion of the radiation beam from reaching the radiation detector; and
   wherein:
      the controller is further operative to regulate the radiation beam via adjusting a thickness of the beam filter while the radiation source and the radiation detector move along the scanning path such that a flux of the radiation beam at the radiation detector is within a target flux range.

2. The system of claim 1, wherein the controller regulates the radiation beam by adjusting at least one of a source current of the radiation source and a source voltage of the radiation source.

3. The system of claim 2 further comprising:
   a data recorder in electronic communication with the controller and operative to store one or more flux-to-variable-control readings that each include:
      a measurement of the flux of the radiation beam at the radiation detector during a duration of time corresponding to the flux-to-variable-control reading; and
      at least one of a measurement of the source current during the duration of time and, a measurement of the source voltage during the duration of time; and
   wherein the controller adjusts at least one of the source current and the source voltage based at least in part on the one or more flux-to-variable-control readings.

4. The system of claim 1, wherein the controller further adjusts the beam filter via adjusting an angle of orientation of the beam filter.

5. The system of claim 4 further comprising:
a data recorder in electronic communication with the controller and operative to store one or more flux-to-variable-control readings that each include:
   a measurement of the flux of the radiation beam at the radiation detector during a duration of time corresponding to the flux-to-variable-control reading; and
   at least one of a measurement of the angle of orientation during the duration of time, and a measurement of the thickness during the duration of time; and
wherein the controller adjusts at least one of the angle of orientation and the thickness based at least in part on the one or more flux-to-variable-control readings.

6. The system of claim 1, wherein the radiation beam is an x-ray beam.

7. The system of claim 6, wherein the x-ray beam includes x-rays of different energy levels.

8. A method for performing a bone density scan of a patient comprising:
emitting a radiation beam via a radiation source that moves along a scanning path and is in electronic communication with a controller;
receiving the emitted radiation beam via a radiation detector that moves along the scanning path and is in electronic communication with the controller;
regulating the radiation beam via the controller such that a flux of the radiation beam at the radiation detector is within a target flux range; and
generating at least one of a bone mineral content measurement of the patient, a bone mineral density measurement of the patient, a body composition measurement of the patient, and a body thickness measurement of the patient via the controller based at least in part on an output signal generated by the radiation detector;
wherein regulating the radiation beam via the controller such that a flux of the radiation beam at the radiation detector is within a target flux range comprises:
   adjusting a thickness of a beam filter via the controller, the beam filter disposed between the radiation source and the radiation detector and operative to restrict a portion of the radiation beam from reaching the radiation detector.

9. The method of claim 8, wherein regulating the radiation beam via the controller such that a flux of the radiation beam at the radiation detector is within a target flux range comprises:
adjusting at least one of a source current of the radiation source and a source voltage of the radiation source via the controller.

10. The method of claim 9 further comprising:
obtaining one or more flux-to-variable-control readings via the controller, each of the flux-to-variable-control readings including:
   a measurement of the flux of the radiation beam at the radiation detector during a duration of time corresponding to the flux-to-variable-control reading; and
   at least one of a measurement of the source current during the duration of time, and a measurement of the source voltage during the duration of time;
storing, via the controller, the one or more flux-to-variable-control readings in a data recorder in electronic communication with the controller; and
wherein adjusting at least one of the source current of the radiation source and the source voltage of the radiation source via the controller is based at least in part on the one or more flux-to-variable-control readings.

11. The method of claim 8, wherein regulating the radiation beam via the controller such that a flux of the radiation beam at the radiation detector is within a target flux range further comprises:
adjusting an angle of orientation of the beam filter.

12. The method of claim 11 further comprising:
obtaining one or more flux-to-variable-control readings via the controller, each of the flux-to-variable-control readings including:
   a measurement of the flux of the radiation beam at the radiation detector during a duration of time corresponding to the flux-to-variable-control reading; and
   at least one of a measurement of the angle of orientation during the duration of time, and a measurement of the thickness during the duration of time;
storing, via the controller, the one or more flux-to-variable-control readings in a data recorder in electronic communication with the controller; and
wherein adjusting at least one of an angle of orientation of the beam filter, and a thickness of the beam filter via the controller is based at least in part on the one or more flux-to-variable-control readings.

13. The method of claim 8, wherein the radiation beam is an x-ray beam.

14. The method of claim 13, wherein the x-ray beam includes x-rays of different energy levels.

* * * * *